(12) United States Patent
Kida et al.

(10) Patent No.: US 8,664,243 B2
(45) Date of Patent: Mar. 4, 2014

(54) SULFONAMIDE COMPOUND AND CRYSTAL THEREOF

(75) Inventors: Hitoshi Kida, Tokyo (JP); Koki Matsubara, Tokyo (JP); Shunsuke Kaneko, Tokyo (JP)

(73) Assignee: Asahi Kasei Pharma Corporation, Tokyo (JP)

(*) Notice: Subject to any disclaimer, the term of this patent is extended or adjusted under 35 U.S.C. 154(b) by 0 days.

(21) Appl. No.: 13/535,116

(22) Filed: Jun. 27, 2012

(65) Prior Publication Data

US 2012/0270898 A1    Oct. 25, 2012

Related U.S. Application Data

(62) Division of application No. 12/216,257, filed on Jul. 1, 2008, now Pat. No. 8,232,292.

(60) Provisional application No. 61/034,222, filed on Mar. 6, 2008.

(30) Foreign Application Priority Data

Jul. 2, 2007 (JP) ................................. 2007/174323

(51) Int. Cl.
  *C07D 401/12* (2006.01)
  *A61K 31/47* (2006.01)

(52) U.S. Cl.
  USPC .......................................... 514/307; 546/139

(58) Field of Classification Search
  None
  See application file for complete search history.

(56) References Cited

U.S. PATENT DOCUMENTS

| | | | |
|---|---|---|---|
| 4,798,897 A | 1/1989 | Hidaka et al. | |
| 5,081,246 A | 1/1992 | Hidaka et al. | |
| 5,216,150 A | 6/1993 | Hidaka et al. | |
| 5,245,034 A | 9/1993 | Hidaka et al. | |
| 5,298,503 A | 3/1994 | Peglion et al. | |
| 6,271,224 B1 | 8/2001 | Kapin et al. | |
| 6,403,590 B1 | 6/2002 | Hellberg et al. | |
| 7,618,984 B2 | 11/2009 | Yamada et al. | |
| 7,964,613 B2 | 6/2011 | Matsubara et al. | |
| 8,232,292 B2 * | 7/2012 | Kida et al. ............ | 514/307 |
| 2004/0102437 A1 | 5/2004 | Takami et al. | |
| 2004/0138286 A1 | 7/2004 | Imazaki et al. | |
| 2005/0020623 A1 | 1/2005 | Yamada et al. | |
| 2005/0096310 A1 | 5/2005 | Yamada et al. | |
| 2005/0272751 A1 | 12/2005 | McKerracher et al. | |
| 2006/0079688 A1 | 4/2006 | Shibuya et al. | |
| 2006/0167043 A1 | 7/2006 | Iwakubo et al. | |
| 2006/0223829 A1 | 10/2006 | Aertgeerts et al. | |
| 2006/0247266 A1 | 11/2006 | Yamada et al. | |
| 2007/0088021 A1 | 4/2007 | Hidaka et al. | |
| 2007/0179127 A1 | 8/2007 | Yamada et al. | |
| 2008/0021018 A1 | 1/2008 | Ohshima et al. | |
| 2009/0048223 A1 | 2/2009 | Matsubara et al. | |

FOREIGN PATENT DOCUMENTS

| | | |
|---|---|---|
| AU | 20675/92 A | 2/1993 |
| CA | 2 506 464 A1 | 3/2004 |
| CA | 2 496 797 A1 | 11/2004 |
| CA | 2 240 271 C | 12/2005 |
| EP | 0 061 673 A1 | 10/1982 |
| EP | 0 287 696 A1 | 10/1988 |
| EP | 0 527 079 A1 | 2/1993 |
| EP | 0 885 888 A1 | 12/1998 |
| EP | 0 956 865 A1 | 11/1999 |
| EP | 1 074 545 A1 | 2/2001 |
| EP | 1 541 151 A1 | 6/2005 |
| EP | 1 568 382 A1 | 8/2005 |
| EP | 1 878 732 A1 | 4/2006 |
| EP | 1 679 308 A1 | 7/2006 |
| EP | 1 902 731 A1 | 3/2008 |
| EP | 1 905 452 A1 | 4/2008 |
| EP | 1 932 841 A1 | 6/2008 |
| JP | 57-156463 A | 9/1982 |
| JP | 57-200366 A | 12/1982 |
| JP | 62-111981 A | 5/1987 |
| JP | 02-256666 A | 10/1990 |
| JP | 04-264030 A | 9/1992 |
| JP | 05-208973 A | 8/1993 |
| JP | 06-100540 A | 4/1994 |
| JP | 10-087491 A | 4/1998 |
| JP | 11-349482 A | 12/1999 |
| JP | 2001-509780 A | 7/2001 |
| JP | 2004-107335 A | 4/2004 |
| JP | 2004-182723 A | 7/2004 |
| JP | 2005-232175 A | 9/2005 |
| JP | 2006-348028 A | 12/2006 |
| JP | 2007-238458 A | 9/2007 |
| WO | WO 93/05014 A1 | 3/1993 |
| WO | WO 97/23222 A1 | 7/1997 |
| WO | WO 97/28130 A1 | 8/1997 |
| WO | WO 98/06433 A1 | 2/1998 |
| WO | WO 99/20620 A1 | 4/1999 |
| WO | WO 99/64011 A1 | 12/1999 |

(Continued)

OTHER PUBLICATIONS

Australian Office Action issued in Australian Patent Application No. 2011253822 on Nov. 27, 2012.

(Continued)

*Primary Examiner* — Zinna Northington Davis

(74) *Attorney, Agent, or Firm* — Birch, Stewart, Kolasch & Birch, LLP

(57) ABSTRACT

(S)-1-(4-Chloro-5-isoquinolinesulfonyl)-3-(methylamino) pyrrolidine monohydrochloride and a crystal thereof, and a crystal of the aforementioned monohydrochloride having a major peak or peaks at one or more positions selected from the group consisting of positions where 2θs are about 13.9°, 21.5°, 21.7°, 22.4°, 22.8°, 24.5° and 35.0° in a powder X-ray diffraction spectrum, which have excellent properties as active ingredient of a medicament for prophylactic and/or therapeutic treatment of glaucoma and the like.

10 Claims, 6 Drawing Sheets

(56) References Cited

FOREIGN PATENT DOCUMENTS

| | | |
|---|---|---|
| WO | WO 01/56988 A1 | 8/2001 |
| WO | WO 02/076976 A2 | 10/2002 |
| WO | WO 02/076977 A2 | 10/2002 |
| WO | WO 02/100833 A1 | 12/2002 |
| WO | WO 2004/009555 A1 | 1/2004 |
| WO | WO 2004/019951 A1 | 3/2004 |
| WO | WO 2004/024717 A1 | 3/2004 |
| WO | WO 2004/045644 A1 | 6/2004 |
| WO | WO 2004/076441 A1 | 9/2004 |
| WO | WO 2004/108724 A1 | 12/2004 |
| WO | WO 2005/011697 A2 | 2/2005 |
| WO | WO 2005/035501 A1 | 4/2005 |
| WO | WO 2005/035503 A1 | 4/2005 |
| WO | WO 2005/035506 A1 | 4/2005 |
| WO | WO 2005/080394 A1 | 9/2005 |
| WO | WO 2006/057397 A1 | 6/2006 |
| WO | WO 2006/115244 A1 | 11/2006 |
| WO | WO 2006/115245 A1 | 11/2006 |
| WO | WO 2006/115247 A1 | 11/2006 |
| WO | WO 2006/137368 A1 | 12/2006 |
| WO | WO 2007/007737 A1 | 1/2007 |
| WO | WO 2007/026664 A1 | 3/2007 |
| WO | WO 2008/105058 | 9/2008 |

OTHER PUBLICATIONS

Morissette et al., "High-throughput crystallization: polymorphs, salts, co-crystals and solvates of pharmaceutical solids", Advanced Drug Delivery Reviews, vol. 56 (2004) pp. 275-300.

A. Ogata, "Kagaku Jikken Sousahou" 1963, p. 281, 386 (with English translation).

A. Suzuki et al., Effects of Calyculin A on Tension and Myosin Phosphorylation in Skinned Smooth Muscle of the Rabbit Mesenteric Artery, Br. J. Pharmacol. (1993) 109, pp. 703-712.

Australian Office Action, in Australian Application No. 2006285915, dated Jun. 2, 2010.

Australian Office Action, in Australian Patent Application No. 2008272396, mailed Dec. 20, 2010.

Canadian Office Action, in Canadian Application No. 2,621,181, dated Feb. 2, 2010.

Chinese Office Action, in Chinese Application No. 200680031607. X, dated Nov. 19, 2010.

Extended European Search Report issued in European Patent Application No. 08790119.5 on Jan. 23, 2012.

Extended European Search Report, in European Application No. 08720915.1, dated Nov. 25, 2010.

Extended European Search Report, in European Application No. 06796896.6, dated Mar. 29, 2011.

Fukata et al., Trends in Pharmacological Sciences, vol. 22, No. 1, pp. 32-39 (Jan. 2001).

G. A. Patani, et al., Bioisosterism: A Rational Approach in Drug Design, Chem. Rev., 1996, vol. 96, pp. 3147-3176.

Indian Office Action, in Indian Application No. 1251/KOLNP/2008, dated Nov. 10, 2010.

International Preliminary Report on Patentability issued in PCT/JP2008/001720 on Feb. 4, 2010.

International Preliminary Report on Patentability, dated Mar. 13, 2008, for Application No. PCT/JP2006/316913.

International Preliminary Report on Patentability, dated Sep. 11, 2009, for Application No. PCT/JP2008/053367.

J. C. Mills et al., Apoptotic Membrane Blebbing is Regulated by Myosin Light Chain Phosphorylation, The Journal of Cell Biology, vol. 140, No. 3, Feb. 9, 1988, pp. 627-636.

J. T. Schmidt et al., Myosin Light Chain Phosphorylation and Growth Cone Motility, J. Neurobiol., vol. 52, No. 3, pp. 175-188 (2002).

K. E. Kamm et al., Regulation of Smooth Muscle Contractile Elements by Second Messengers, Annu. Rev. Physiol., vol. 51, pp. 299-313 (1989).

K. Itoh et al., Diphosphorylation of Platelet Myosin Ex Vivo in the Initial Phase of Activation by Thrombin, Biochimica et Biophysica Acta, 1136, (1992), pp. 52-56.

Korean Notice of Final Rejection, dated Nov. 29, 2010, for Korean Application No. 10-2008-7007566.

Korean Office Action, dated Mar. 22, 2010, for Korean Application No. 10-2008-7007566.

M. Barany et al., Protein Phosphorylation During Contraction and Relaxation, Biochemistry of Smooth Muscle Contraction, pp. 321-339, (1996).

M. Tamura et al., Development of Specific Rho-Kinase Inhibitors and their Clinical Application, Biochimica et Biophysica Acta, 1754 (2005) 245-252.

M. Uehata, et al., Calcium Sensitization of Smooth Muscle Mediated by a Rho-associated Protein Kinase in Hypertension, Nature, vol. 389, pp. 990-994 (1997).

Mexican Office Action, in Mexican Application No. MX/a/2008/002838, dated Mar. 7, 2011.

Mexican Official Action, dated Oct. 19, 2010, for Mexican Application No. MX/a/2008/002838.

Notice of Allowance/Notice of Allowability issued Dec. 24, 2008, in U.S. Appl. No. 11/511,395.

Notice of Allowance/Notice of Allowability issued Jun. 29, 2009, in U.S. Appl. No. 11/511,395.

P. H. Howe et al., Purification and Characterization of Protein Kinase C from Rabbit Iris Smooth Muscle, Biochem J. (1988) 255, pp. 423-429.

P. L. Mobley et al., Decreased Phosphorylation of Four 20-kDa Proteins Precedes Staurosporine-Induced Disruption of the Actin/Myosin Cytoskeleton in Rat Astrocytes1, Experimental Cell Research, 214, pp. 55-66, (1994).

Restriction Requirement of Sep. 8, 2008, in U.S. Appl. No. 11/511,395.

S. Kitani et al., Inhibition of IgE-Mediated Histamine Release by Myosin Light Chain Kinase Inhibitors, Biochemical and Biophysical Research Communications, vol. 183, No. 1, pp. 48-54 (1992).

Specification of U.S. Appl. No. 12/071,921, filed Feb. 27, 2008.

T. Ito, et al., RHO Inhibitor Improves Motor Dysfunction and Hypoalgesia in Rat Model of Lumbar Spinal Canal Stenosis, 52nd Meeting of the Orthopedic Research Society, Paper No. 1870 (2006).

T. Ito, et al., RHO Kinase Inhibitor Improves Motor Dysfunction and Hypoalgesia in a Rat Model of Lumbar Spinal Canal Stenosis, Spine, vol. 32. No. 19, pp. 2070-2075 (2007).

V. Niggli, RHO-Kinase in Human Neutrophils: A Role in Signaling for Myosin Light Chain Phosphorylation and Cell Migration, FEBS Letters, 445 (1999) pp. 69-72.

\* cited by examiner

SULFONAMIDE COMPOUND AND CRYSTAL THEREOF

CROSS REFERENCE TO RELATED APPLICATIONS

This application is a Divisional of application Ser. No. 12/216,257 filed on Jul. 1, 2008, now U.S. Pat. No. 8,232,292, which claims the benefit of U.S. Provisional Application No. 61/034,222 filed on Mar. 6, 2008 under 35 U.S.C. §119(e), and to Patent Application No. 2007-174323 filed in Japan, on Jul. 2, 2007 under 35 U.S.C. §119(a)-(d). The entire contents of all of the above applications is hereby incorporated by reference.

TECHNICAL FIELD

The present invention relates to a novel sulfonamide compound and a salt thereof. More specifically, the present invention relates to (S)-1-(4-chloro-5-isoquinolinesulfonyl)-3-(methylamino)pyrrolidine, monohydrochloride thereof and monohydrobromide thereof useful as active ingredients of medicaments.

BACKGROUND ART

Sulfonamide derivatives which inhibit phosphorylation of myosin regulatory light chain and have an intraocular pressure reducing action and neutrophil migration inhibitory action are known (International Publication WO2007/026664), and it has been elucidated that these sulfonamide derivatives are useful as active ingredients of medicaments for prophylactic and/or therapeutic treatment of glaucoma and the like.

However, (S)-1-(4-chloro-5-isoquinolinesulfonyl)-3-(methylamino)pyrrolidine in free base represented by the following formula (1) is not disclosed in International Publication WO2007/026664 (hereinafter in the specification, this compound in a free base may be referred to as "Compound 1").

[Formula 1]

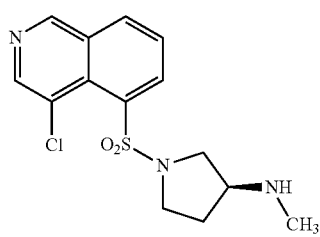

(1)

Hydrochloride of Compound 1 mentioned above is disclosed in International Publication WO2007/026664, and this hydrochloride is prepared by treating tert-butoxycarbonylated Compound 1 with excessive hydrochloric acid and removing the tert-butoxycarbonyl group (Example 19-3). However, the aforementioned publication discloses only the preparation method, and no description is given as for number of hydrochloric acid molecules added to the resulting (S)-1-(4-chloro-5-isoquinolinesulfonyl)-3-(methylamino)pyrrolidine hydrochloride, physicochemical properties of the resulting hydrochloride and the like.

Patent document 1: WO2007/026664

DISCLOSURE OF THE INVENTION

Object to be Achieved by the Invention

For use of (S)-1-(4-chloro-5-isoquinolinesulfonyl)-3-(methylamino)pyrrolidine as an active ingredient of a medicament, an object of the present invention is to provide a novel salt form thereof having more preferred properties.

Means for Achieving the Object

The inventors of the present invention precisely conducted reproductive experiment of the method described in Example 19-3 of the aforementioned International Publication WO2007/026664 to prepare hydrochloride of (S)-1-(4-chloro-5-isoquinolinesulfonyl)-3-(methylamino)pyrrolidine described in the above publication, and conducted researches on the structure and physicochemical properties of the substance. As a result, they found that the hydrochloride was a salt having two hydrochloric acids added, i.e., (S)-1-(4-chloro-5-isoquinolinesulfonyl)-3-(methylamino)pyrrolidine dihydrochloride (hereinafter in the specification, this substance is sometimes referred to as "dihydrochloride"). They also found that changes in physicochemical properties of the dihydrochloride were observed after stability test at 60° C. for two weeks, and that the hydrochloride gave remarkable hygroscopicity as well as the changes in physicochemical properties after storage for two weeks under the conditions of 25° C. and 84% RH.

Generally as for substances as active ingredients of medicaments, it is known that chemical or physical stability of the substances significantly influence on effectiveness and safety of the medicaments. Therefore, especially in industrial scale production, it is desirable to use a substance that is more stable against temperature or humidity as an active ingredient of a medicament. By using such a stable substance, reduction of content of an active ingredient during storage or distribution of a medicament can be prevented, and thus a medicament that can ensure effectiveness and safety over a long period of time can be supplied.

From the viewpoint as mentioned above for use of the above Compound 1 as a medicament, the inventors of the present invention conducted researches in order to provide a substance in a form of a salt having more preferred properties, especially more improved properties in stability and hygroscopicity than the aforementioned dihydrochloride. As a result, it was found that both of (S)-1-(4-chloro-5-isoquinolinesulfonyl)-3-(methylamino)pyrrolidine monohydrochloride (hereinafter in the specification, this substance is sometimes referred to as "monohydrochloride") and (S)-1-(4-chloro-5-isoquinolinesulfonyl)-3-(methylamino)pyrrolidine monohydrobromide (hereinafter in the specification, this substance is sometimes referred to as "monohydrobromide") had good stability and reduced hygroscopicity. The present invention was accomplished on the basis of the aforementioned findings.

The present invention thus provides the following substances.

(1) (S)-1-(4-Chloro-5-isoquinolinesulfonyl)-3-(methylamino)pyrrolidine monohydrochloride.
(2) (S)-1-(4-Chloro-5-isoquinolinesulfonyl)-3-(methylamino)pyrrolidine monohydrobromide.
(3) A crystal of (S)-1-(4-chloro-5-isoquinolinesulfonyl)-3-(methylamino)pyrrolidine.
(4) A crystal of (S)-1-(4-chloro-5-isoquinolinesulfonyl)-3-(methylamino)pyrrolidine monohydrochloride.
(5) A crystal of (S)-1-(4-chloro-5-isoquinolinesulfonyl)-3-(methylamino)pyrrolidine monohydrobromide.
(6) The crystal of (S)-1-(4-chloro-5-isoquinolinesulfonyl)-3-(methylamino)pyrrolidine according to (3), which has a major peak or peaks at one or more positions selected from the group consisting of positions where 2θs are about 9.1°, 13.8°, 21.0°, 21.7° and 23.6° in a powder X-ray diffraction spectrum.
(7) The crystal of (S)-1-(4-chloro-5-isoquinolinesulfonyl)-3-(methylamino)pyrrolidine according to (3) or (6), which has major peaks at position where 2θs are about 9.1°, 13.8°, 21.0°, 21.7° and 23.6° in a powder X-ray diffraction spectrum.
(8) The crystal of (S)-1-(4-chloro-5-isoquinolinesulfonyl)-3-(methylamino)pyrrolidine according to (3), (6) or (7), which has major peaks at positions where wave numbers are about 1335, 1146, 1139, 1096 and 609 $cm^{-1}$ in an infrared absorption spectrum.
(9) The crystal of (S)-1-(4-chloro-5-isoquinolinesulfonyl)-3-(methylamino)pyrrolidine according to (3), (6), (7) or (8), which has a fusion peak at about 106° C. in differential scanning calorimetry (temperature increasing rate: 10° C./minute).
(10) The crystal of (S)-1-(4-chloro-5-isoquinolinesulfonyl)-3-(methylamino)pyrrolidine monohydrochloride according to (4), which has a major peak or peaks at one or more positions selected from the group consisting of positions where 2θs are about 13.9°, 21.5°, 21.7°, 22.4°, 22.8°, 24.5° and 35.0° in a powder X-ray diffraction spectrum.
(11) The crystal of (S)-1-(4-chloro-5-isoquinolinesulfonyl)-3-(methylamino)pyrrolidine monohydrochloride according to (4) or (10), which has major peaks at positions where 2θs are about 13.9°, 21.5°, 21.7°, 22.4°, 22.8°, 24.5° and 35.0° in a powder X-ray diffraction spectrum.
(12) The crystal of (S)-1-(4-chloro-5-isoquinolinesulfonyl)-3-(methylamino)pyrrolidine monohydrochloride according to (4), (10) or (11), which shows major peaks at positions where wave numbers are about 1330, 1150, 1140 and 613 $cm^{-1}$ in an infrared absorption spectrum.
(13) The crystal of (S)-1-(4-chloro-5-isoquinolinesulfonyl)-3-(methylamino)pyrrolidine monohydrochloride according to (4), (10), (11) or (12), which has a decomposition peak at about 290° C. in differential scanning calorimetry (temperature increasing rate: 10° C./minute).
(14) The crystal of (S)-1-(4-chloro-5-isoquinolinesulfonyl)-3-(methylamino)pyrrolidine monohydrobromide according to (5), which has a major peak or peaks at one or more positions selected from the group consisting of positions where 2θs are about 21.3°, 22.4°, 24.1°, 30.7° and 34.8° in a powder X-ray diffraction spectrum.
(15) The crystal of (S)-1-(4-chloro-5-isoquinolinesulfonyl)-3-(methylamino)pyrrolidine monohydrobromide according to (5) or (14), which has major peaks at positions where 2θs are about 21.3°, 22.4°, 24.1°, 30.7° and 34.8° in a powder X-ray diffraction spectrum.
(16) The crystal of (S)-1-(4-chloro-5-isoquinolinesulfonyl)-3-(methylamino)pyrrolidine monohydrobromide according to (5), (14) or (15), which has major peaks at positions where wave numbers are about 2695, 1307, 1149, 1139 and 612 $cm^{-1}$ in an infrared absorption spectrum.
(17) The crystal of (S)-1-(4-chloro-5-isoquinolinesulfonyl)-3-(methylamino)pyrrolidine monohydrobromide according to (5), (14), (15) or (16), which has a decomposition peak at about 270° C. in differential scanning calorimetry (temperature increasing rate: 10° C./minute).
(18) A method for preparing the crystal of (S)-1-(4-chloro-5-isoquinolinesulfonyl)-3-(methylamino)pyrrolidine according to any one of (3) and (6) to (9), which comprises the steps of adding a base to an acidic solution containing (S)-1-(4-chloro-5-isoquinolinesulfonyl)-3-(methylamino)pyrrolidine to neutralize the solution wherein the compound is prepared by reacting (S)-3-[N-(tert-butoxycarbonyl)-N-methylamino]-1-(4-chloro-5-isoquinolinesulfonyl) pyrrolidine with an acid in a solvent, and isolating deposited solid.
(19) A method for preparing the crystal of (S)-1-(4-chloro-5-isoquinolinesulfonyl)-3-(methylamino)pyrrolidine according to any one of (3) and (6) to (9), which comprises the steps of adding a base to a solution of dihydrohalide of (S)-1-(4-chloro-5-isoquinolinesulfonyl)-3-(methylamino)pyrrolidine to neutralize the solution and thereby prepare (S)-1-(4-chloro-5-isoquinolinesulfonyl)-3-(methylamino) pyrrolidine, and isolating a solid of the compound deposited in a poor solvent in which the compound is hardly dissolved.
(20) A method for preparing the crystal of (S)-1-(4-chloro-5-isoquinolinesulfonyl)-3-(methylamino)pyrrolidine monohydrochloride according to any one of (4) and (10) to (13), which comprises the steps of adding 0.5 to 2 equivalents of hydrochloric acid to a solution in which (S)-1-(4-chloro-5-isoquinolinesulfonyl)-3-(methylamino)pyrrolidine is dissolved, and isolating a deposited crystal.
(21) A method for preparing the crystal of (5)-1-(4-chloro-5-isoquinolinesulfonyl)-3-(methylamino)pyrrolidine monohydrobromide according to any one of (5) and (14) to (17), which comprises the steps of adding 0.5 to 2 equivalents of hydrobromic acid to a solution in which (S)-1-(4-chloro-5-isoquinolinesulfonyl)-3-(methylamino)pyrrolidine is dissolved, and isolating a deposited crystal.
(22) A pharmaceutical composition comprising (S)-1-(4-chloro-5-isoquinolinesulfonyl)-3-(methylamino)pyrrolidine monohydrochloride or (S)-1-(4-chloro-5-isoquinolinesulfonyl)-3-(methylamino)pyrrolidine monohydrobromide as an active ingredient.
(23) A pharmaceutical composition comprising the crystal according to any one of (4) and (10) to (13) as an active ingredient.
(24) A pharmaceutical composition comprising the crystal according to any one of (5) and (14) to (17) as an active ingredient.
(25) A composition comprising the monohydrochloride, wherein mass ratio of the monohydrochloride is about 20% or more based on the total mass of (S)-1-(4-chloro-5-isoquinolinesulfonyl)-3-(methylamino)pyrrolidine, salt thereof and solvate thereof, which is taken as 100%.

Effect of the Invention (S)-1-(4-Chloro-5-isoquinolinesulfonyl)-3-(methylamino)pyrrolidine monohydrochloride and (S)-1-(4-chloro-5-isoquinolinesulfonyl)-3-(methylamino)pyrrolidine monohydrobromide provided by the present invention have a characteristic feature that they are more stable and less hygroscopic compared with the dihydrochloride prepared by the method described in Example 19-3 of International Publication WO2007/026664. Therefore, by using these substances as active ingredients of medicaments, medicaments can be provided in which reduction of a content of active ingredient during storage or distribution is suppressed, and medicaments can be stably supplied of which effectiveness and safety can be ensured over a long period of time.

BEST MODE FOR CARRYING OUT THE INVENTION

Figure 1:
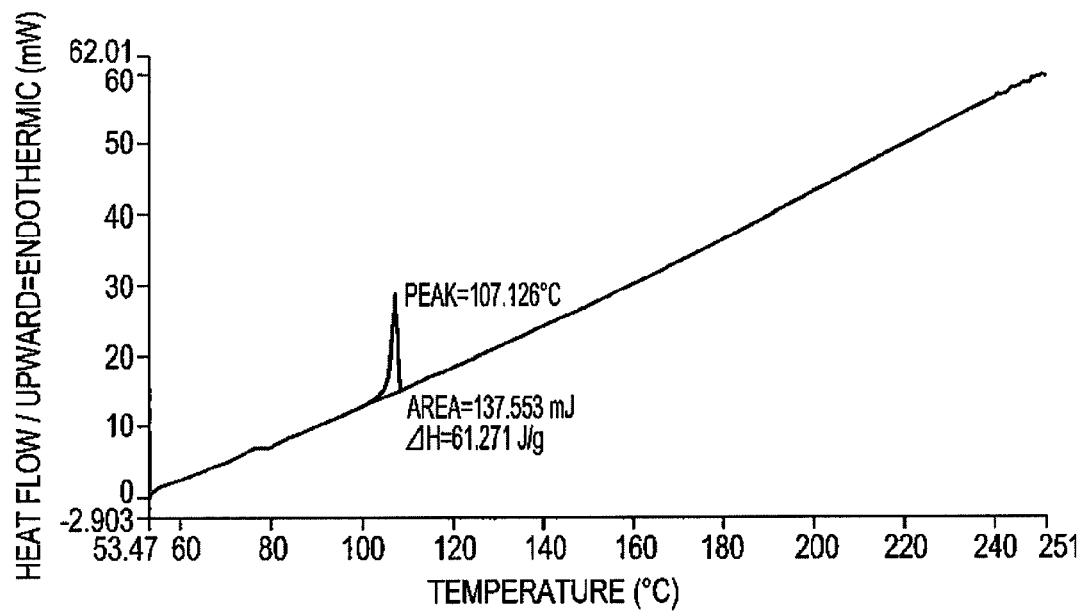
FIG. 1 A figure depicting differential scanning calorimetry spectrum of Compound 1 obtained by a method similar to the method described in Example 1

This application is a patent application filed with claiming conventional priorities based on Japanese Patent Application No. 2007.174323 filed in Japan on Jul. 2, 2007 and Provisional Patent Application No. 61/034,222 filed in the United States on Mar. 6, 2008. The entire disclosures of the specifications, claims, and drawings of these applications are incorporated in the disclosure of the present specification by reference.

Compound 1 can be prepared by, for example, reacting (S)-3-[N-(tert-butoxycarbonyl)-N-methylamino]-1-(4-chloro-5-isoquinolinesulfonyl)pyrrolidine obtainable by the method described in WO2007/026664 with a large excess amount of an acid in a solvent to remove the tert-butoxycarbonyl group, then adding a base to the solution, and isolating deposited solid.

As the solvent used for the removal of the tert-butoxycarbonyl group, for example, water, alcohols such as methanol, ethanol and 2-propanol, ethers such as tetrahydrofuran and 1,4-dioxane, esters such as ethyl acetate and isopropyl acetate, acetonitrile, dichloromethane and the like are preferred, and they can be used as a mixture if needed. Among them, methanol, ethanol and 2-propanol are more preferred. Use of a mixture of water and 2-propanol is particularly preferred. The mixing ratio of water and 2-propanol is, for example, about 1:10 to 10:1, more preferably 1:1 to 10:1, particularly preferably 2:1 to 6:1.

Type of the acid used for the removal of tert-butoxycarbonyl group is not particularly limited, and ordinarily used mineral acids, organic acid and the like may be used. For example, hydrochloric acid, sulfuric acid, nitric acid, hydrobromic acid, phosphoric acid and trifluoroacetic acid are preferred, hydrochloric acid and trifluoroacetic acid are more preferred, and hydrochloric acid is particularly preferred.

Amount of the acid used for the removal of tert-butoxycarbonyl group is not particularly limited, and the acid may be added to such an extent that the removal reaction sufficiently proceeds. The amount may be, for example, 2 equivalents or more, more preferably 2.0 to 10.0 equivalents, particularly preferably 2.0 to 5.0 equivalents, based on Compound 1.

As the reaction temperature, a suitable temperature of, for example, from 10° C. to the reflux temperature of the solvent may be chosen, and a preferred example is a temperature of from 30 to 70° C. The reaction time is, for example, usually about 0.1 to 24 hours, more preferably 0.5 to 10 hours, particularly preferably 1 to 5 hours. Progress of the reaction can be monitored by thin layer chromatography (TLC), high performance liquid chromatography (HPLC) or the like, and an acidic solution of Compound 1 can be prepared usually by appropriately terminating the reaction when the yield of Compound 1 reaches to the maximum.

Although type of the base added to the acidic solution of Compound 1 to deposit Compound 1 produced is not particularly limited, for example, an inorganic base is preferred. Examples of the inorganic base include, for example, alkali metal bases such as sodium hydroxide, potassium hydroxide, sodium carbonate, potassium carbonate, sodium hydrogencarbonate, sodium methoxide and potassium t-butoxide and the like, sodium hydroxide, potassium hydroxide and the like are more preferred, and sodium hydroxide is particularly preferred. These bases, per se, can be used as solid, or they can also be used by being dissolved beforehand in water or an alcohol such as methanol, ethanol, or 2-propanol. By preparing an aqueous solution containing a base at a given concentration beforehand and using the solution, an advantage is enjoyed that an amount of the base to be added may be easily adjusted.

As the crystallization solvent used for depositing Compound 1, for example, water, alcohols such as methanol, ethanol and 2-propanol, ethers such as tetrahydrofuran, esters such as ethyl acetate and isopropyl acetate, acetonitrile, dichloromethane and the like are preferred, and a mixture of these solvents can be used if needed. Among them, water, methanol, ethanol, and 2-propanol are more preferred. Further, use of a mixture of water and 2-propanol is particularly preferred. An example of a mixing ratio of water and 2-propanol includes, for example, about 1:10 to 10:1. A ratio of 1:1 to 10:1 is more preferred, and 2:1 to 6:1 is particularly preferred. When a solvent different from the reaction solvent used for the removal of tert-butoxycarbonyl group is used as a solvent for the crystallization, the solvent can be replaced by concentration or the like.

Although an amount of the base to be added is not particularly limited and the base may be added in an amount providing a good yield of Compound 1 as a solid. Generally, an example includes about 1 equivalent or more based on 1 equivalent of the acid added. It is also possible to select the amount of the base to be added depending on a pH of the solution. Generally, it is preferable to adjust a pH of the solution to be 7 or higher, and more preferred example includes a pH of from 8 to 12.

Temperature of the solution at the time of adding the base is not particularly limited so far that the temperature is an appropriate temperature of from 0° C. to the boiling point of the solution. A temperature in the range of 10 to 40° C. is more preferred.

Although deposition concentration of Compound 1 after the addition of the base may vary depending on the type of a solvent used or depending on a mixing ratio of solvents in a case of a mixed solvent, a lower limit includes, for example, generally 1 w/v % or higher, preferably 5 w/v % or higher. As an upper limit, 30 w/v % or lower is preferred, and more preferred example includes 15 w/v % or lower. For example, when a mixed solvent of water and 2-propanol is used as the solvent, it is preferred that the ratio thereof is 4:1 to 6:1 and the deposition concentration is from 5 w/v % to 10 w/v %, and more preferred example includes about 8 w/v %.

For deposition of a solid of Compound 1, another preferred embodiment includes the addition of a small amount of Compound 1 as seed crystals to a solution after the addition of a base.

Examples of the method for isolating Compound 1 deposited include known methods such as filtration and decantation. It is usually preferable to conduct isolation by filtration. Although the isolation of Compound 1 by filtration may also be performed immediately after the addition of a base, the isolation is preferably performed after the deposition of solid reaches to a stationary state. For example, the isolation is preferably performed 1 hour after the addition of the base, more preferably performed 3 hours after the addition of the base.

At the time of isolating Compound 1 deposited, it is also possible to cool the solution after the addition of the base and then perform the isolation. Examples of the method for cooling include a method of cooling rapidly, a method of cooling step by step, a method of cooling gradually over a period of time, a method of standing the solution for cooling and the like, and the method of cooling step by step, the method of cooling gradually over a period of time, and the method of standing the solution for cooling are more preferred. Generally, a cooling temperature is preferably from 0 to 20° C., and more preferably from 0 to 10° C.

Compound 1 isolated can be dried by a drying method ordinarily performed, for example, drying under reduced pressure, drying by warming under reduced pressure, drying by warming with ventilation, air drying and the like. The drying by warming under reduced pressure and the drying by warming with ventilation are particularly preferred. When warming is applied for the drying, a temperature of room temperature or higher is usually chosen. A temperature of from 40 to 60° C. is more preferred. As for time period for the drying, drying may be performed until residual level of a solvent becomes appropriate. For example, 10 hours or longer is preferred.

Among the preparation methods described above, a preferred embodiment includes the following method.

An acidic solution of Compound 1 is prepared by adding (S)-3-[N-(tert-butoxycarbonyl)-N-methylamino]-1-(4-chloro-5-isoquinolinesulfonyl)pyrrolidine and hydrochloric acid in an amount of 3.0 equivalents based on the compound to a mixed solvent of water and 2-propanol at a mixing ratio of 2:1 to 6:1 and performing a reaction at a temperature of 50 to 65° C. for 1 to 3 hours with stirring. The acidic solution is added with sodium hydroxide at a temperature of 20 to 35° C. with stirring to adjust a pH at from 8 to 10, then the solution is further stirred for 1 to 20 hours, and deposited solid is isolated. By drying the isolated solid under reduced pressure at 50° C. for 10 hours or longer, crystals of Compound 1 are obtained.

Compound 1 can also be isolated by dissociating the added hydrochloric acids from the dihydrochloride obtained according to the method described in Example 19-3 of WO2007/026664 by a reaction with a base in an appropriate solvent to prepare a solution containing Compound 1, then removing the solvent by concentration, and adding a poor solvent in which Compound 1 is hardly dissolved to the residue to deposit Compound 1.

As the reaction solvent used for the dissociation of the hydrochloric acid from the dihydrochloride, for example, water, alcohols such as methanol, ethanol and 2-propanol, ethers such as tetrahydrofuran and 1,4-dioxane, esters such as ethyl acetate and isopropyl acetate, acetonitrile, dichloromethane and the like are preferred, and a mixture of these solvents may be used if needed. Among them, water, methanol, ethanol and 2-propanol are more preferred, and water is particularly preferred.

As the base added for a purpose of dissociating the hydrochloric acid from the dihydrochloride, the base added to the acidic solution of Compound 1 can be used. Generally, an amount of the base to be added is preferably 1.6 equivalents or more, more preferably 2 to 4 equivalents, based on 1 equivalent of the dihydrochloride. A temperature of the solution at the time of adding the base is not particularly limited so far that the temperature is an appropriate temperature of from 0° C. to the boiling point of the solution. A range of 5 to 25° C. is more preferred. As for the method of adding the base, the base can usually be added at one portion with stirring the solution. The base may be added several times as divided portions or continuously added over a period of time by a method such as dropping or the like.

For the removal of a solvent by concentration, it is also possible to conduct substitution with a solvent having a lower boiling point beforehand such as by extraction and then perform the concentration. A preferred example includes, for example, a method of extracting Compound 1 with an organic solvent such as dichloromethane from the aqueous solution containing Compound 1 prepared by the aforementioned method and evaporating dichloromethane under reduced pressure.

Examples of the poor solvent (i.e., a solvent in which Compound 1 is hardly dissolved) added to deposit Compound 1 from the residue include water, ethyl acetate, n-hexane, n-heptane, diisopropyl ether and the like, and ethyl acetate and n-hexane are more preferred. These solvents can also be used as a mixture if needed.

Compound 1 deposited can be isolated by the method explained above, and can be dried if needed.

The structure of Compound 1 can be confirmed on the basis of $^1$H-$^1$H correlation, $^{13}$C-$^{13}$C correlation, $^1$H-$^{13}$C correlation and the like in a nuclear magnetic resonance spectrum and/or analysis of mass spectrum. For example, the structure can be confirmed on the basis of $^1$H-$^1$H correlation in a nuclear magnetic resonance spectrum, and the (m/Z) value of the protonated compound (326) in a mass spectrum.

The monohydrochloride can be prepared by adding hydrochloric acid to a solution in which Compound 1 is dissolved, and isolating deposited crystals. Compound 1 may be in the form of either crystal or amorphous, or a mixture thereof. As the solvent for dissolving Compound 1, alcohols such as methanol, ethanol, 1-propanol and 2-propanol, ethers such as tetrahydrofuran and 1,4-dioxane, esters such as ethyl acetate and isopropyl acetate, acetone, acetonitrile and the like are preferred, and these solvents can be used as a mixture if needed. Among them, methanol, ethanol, 1-propanol and 2-propanol are more preferred, and ethanol and 2-propanol are particularly preferred. These solvents may contain water at a ratio of about 30% or less in terms of volume ratio.

An amount of the solvent added for dissolving Compound 1 by using the solvents as mentioned above may vary depending on the type of the solvent used and a mixing ratio in case of a mixed solvent. An amount wherein Compound 1 is dissolved at a temperature below the boiling point of the solvent used is preferred, and further from a viewpoint of an yield of crystals obtained, use of an amount wherein Compound 1 is dissolved and to give a saturation concentration at a temperature near the boiling point of the solvent is particularly preferred. More specifically, when 2-propanol is used as the solvent, for example, a method of adding 100 to 200 ml of 2-propanol to 10 g of Compound 1 and warming the mixture to 60° C. or higher is preferred, and when ethanol is used, a preferred example includes a method of adding 70 to 150 ml of ethanol to 10 g of Compound 1 and warming the mixture to 60° C. or higher. When insoluble solids exist, it is preferred to remove the insoluble solids from the solution by an operation such as filtration or the like.

As for an amount of hydrochloric acid added to the aforementioned solution to deposit the crystals of the monohydrochloride, a range of from 0.5 to 2 equivalents is generally preferred based on Compound 1. A range of from 0.8 to 1.5 equivalents is more preferred, 0.9 to 1.2 equivalents is particularly preferred. A most particularly preferred example includes 0.95 to 1.05 equivalents. When a solvent is chosen from which the monohydrochloride is preferentially deposited, it is also possible to add 2 equivalents or more of hydrochloric acid. For example, when ethanol or 2-propanol is chosen as the solvent, a preferred example includes a range of from 0.5 to 10 equivalents as the amount of hydrochloric acid, and a more preferred example includes a range of 0.5 to 5 equivalents. Hydrochloric acid to be added can be used after being dissolved in water or the aforementioned solvents. A use of an aqueous hydrochloric acid solution prepared beforehand at a given concentration is preferred from a viewpoint of convenience of controlling the amount to be added.

Although a temperature at the time of adding the hydrochloric acid is not particularly limited so far that the temperature is an appropriate temperature of from 0° C. to the boiling point of the solution, a temperature that gives saturated concentration of Compound 1 or higher is preferred. Specifically, when 10 g of the compound is dissolved in 100 to 200 ml of 2-propanol, for example, it is preferable to add 5 N aqueous hydrochloric acid at 40 to 60° C.

A method for adding hydrochloric acid is not particularly limited. Generally, the acid may be added as one portion with stirring the solution, or the acid may be added several times as divided portions, or continuously added over a period of time by a method such as dropping or the like.

For deposition of crystals, preferred embodiments include a method of adding a small amount of crystals of the monohydrochloride as seed crystals to the solution after addition of hydrochloric acid, and a method of cooling the solution after addition of hydrochloric acid. Examples of the method for cooling include a method of cooling rapidly, a method of cooling step by step, a method of cooling gradually over a period of time, a method of standing the solution for cooling and the like. More preferred examples include the method of cooling step by step, the method of cooling gradually over a period of time, and the method of standing the solution for cooling.

A final concentration of the monohydrochloride at the time of the deposition of crystals after the addition of hydrochloric acid may vary depending on type of the solvent used and a mixing ratio in the case of a mixed solvent. An example of a lower limit generally includes 0.5 w/v % or higher, more preferable example includes 1 w/v % or higher. A preferred example of an upper limit includes 20 w/v % or lower, and more preferred example includes 10 w/v % or lower. Specifically, for example, when a mixed solvent of water and 2-propanol (mixing ratio is 1:9 to 0.5:9.5) is used as the solvent for deposition, a final concentration of 2.5 to 10 w/v % is preferred, and more preferred example includes 5 to 7.5 w/v %.

Examples of the method for isolating deposited crystals include known methods such as filtration and decantation. Generally, isolation by filtration is preferred. Although the isolation of the crystals may be performed immediately after the addition of hydrochloric acid, the isolation is preferably performed after the deposition of crystals reaches to a stationary state. For example, the isolation is preferably performed 1 hour after the addition, and more preferably performed 3 hours after the addition.

For collection of the deposited crystals, collection of the crystals after cooling of the solution in which deposition of crystals reaches to a stationary state is preferred from a viewpoint of an yield of the crystals to be obtained and the like. Examples of the method for cooling include a method of cooling rapidly, a method of cooling step by step, a method of cooling gradually over a period of time, a method of standing the solution for cooling and the like. The method of cooling step by step, the method of cooling gradually over a period of time, and the method of standing the solution for cooling are more preferred. As a cooling temperature, a temperature of from 0 to 20° C. is generally preferred, and 0 to 10° C. is more preferred.

After the crystals are isolated by filtration, the crystals can be washed with the solvent used for dissolving Compound 1, for example, ethanol, 2-propanol or a mixed solvent of water therewith, which is an effective operation for removing impurities. Examples of the method for washing include a method of rinsing the crystals on a filter with a solvent, and a method of putting the crystals into a solvent to form a suspension, sufficiently stirring the suspension, and then collecting the crystals again by filtration. Furthermore, it is also effective to perform both of the aforementioned two kinds of washing operations.

The collected crystals can be dried by a drying method ordinarily performed, for example, drying under reduced pressure, drying by warming under reduced pressure, drying by warming with ventilation, air drying and the like.

Among the aforementioned preparation methods, a preferred example includes a method of warming a suspension of Compound 1 in 2-propanol to 50 to 60° C. to dissolve Compound 1, adding dropwise 1 equivalent of hydrochloric acid based on Compound 1 to the solution at 20 to 60° C. with stirring, and further stirring for 1 to 20 hours to obtain crystals.

The monohydrobromide can be prepared by adding hydrobromic acid to a solution in which Compound 1 is dissolved, and isolating deposited crystals. This method can be performed in the same manner as that of the aforementioned method for preparing the monohydrochloride by using hydrobromic acid instead of hydrochloric acid.

For evaluating the type of the acid forming a salt with Compound 1 and the number of the acid added, ion exchange chromatography is applied to calculate the number of the acid added per Compound 1. For example, a method comprises calculation of the number of the added acid per Compound 1 by dissociating the added acid by ion exchange using an ion exchange column such as DIONEX IonPacAS14 with an internal diameter of 4 mm and a length of 25 cm, and comparing peak areas with those of standard solutions of known ion concentrations by using an electric conductivity detector to quantify the acid.

Further, the type of the acid forming a salt with Compound 1 and the number of the acid added can also be evaluated by other means such as quantification of amounts of elements by elemental analysis. Furthermore, if the substance consists of a single kind of crystal, the type of the acid forming a salt with Compound 1 and the number of acid added can also be evaluated by X-ray structure analysis.

It is well-known to those skilled in the art that the number of added acid measured by ion chromatography may include some measurement errors due to various kinds of factors. As for the number of the added acid per Compound 1, a measurement error of ±0.2 is usually acceptable, and a measurement error of ±0.1 is acceptable for a more preferred measurement.

As a confirmation test of the monohydrochloride or the monohydrobromide (hereinafter these substances are also referred to as "substance in the form of a salt"), powder X-ray diffractometry may also be used. Furthermore, an infrared absorption spectrum may be measured. More specifically, an example of the method includes a method of measuring an infrared absorption spectrum by using powder. For example, the potassium bromide tablet method described in Japanese Pharmacopoeia, General Test Methods, "Infrared Absorption Spectrometry" can be chosen.

For evaluation of purity of Compound 1 or the substance in the form of a salt, the area percentage method based on HPLC is convenient. For evaluation of water content of Compound 1 or the substance in the form of a salt, the volumetric titration method, the coulometric titration method described in Japanese Pharmacopoeia, General Test Methods, "Water Determination", the loss on drying test and the like can be used. When sample weight is small, the coulometric titration method can be preferably chosen.

When it is necessary to measure an amount of Compound 1 or the substance in the form of a salt contained in a pharmaceutical preparation, use of HPLC is usually convenient and thus preferred. For example, a calibration curve can be prepared by HPLC using standard samples of Compound 1 having known chemical purities, and amount of Compound 1 existing in a sample can be determined on the basis of the calibration curve.

Examples of an optical system used for the powder X-ray diffraction spectrometry include an ordinary light concentrating type optical system and a parallel beam type optical system. Although the optical system to be used is not particularly limited, when resolution and intensity are desired to be ensured, the measurement is preferably performed by using a light concentrating type optical system. Further, when orientation is desired to be suppressed, which is a phenomenon that molecules are arranged along a certain direction depending on shapes of crystals (needle shape, tabular shape and the like), the measurement is preferably performed by using a parallel beam type optical system. Examples of measurement apparatus of the light concentrating type optical system include XRD-6000 (Shimadzu), MultiFlex (Rigaku International) and the like. Examples of measurement apparatus of the parallel beam type optical system include XRD-7700 (Shimadzu), RINT2200 Ultima+/PC (Rigaku International) and the like.

It is well-known to those skilled in the art that 2θ values in a powder X-ray diffraction spectrum may include some measurement errors due to various kinds of factors. A measurement error of usually about ±0.3°, typically about ±0.2°, or about ±0.1° for a more preferable measurement, is acceptable. Therefore, it will be understood by those skilled in the art that values indicated in the specification with the term "about" for 2θ values may include an acceptable measurement error.

Although it is well-known to those skilled in the art that a measured value obtained by differential scanning calorimetry is a numerical value characteristic to crystals as a measurement object, it is also well-known to those skilled in the art that, besides measurement errors, melting point may occasionally change in a practical measurement due to various causes such as contamination of an acceptable amount of impurities. Therefore, those skilled in the art can understand that the peak temperatures mentioned in the specification practically measured in differential scanning calorimetry may occasionally change, and that a degree of the change may be, for example, about ±5° C., typically about ±3° C., or about ±2° C. for preferred measurement. Examples of measurement apparatus used for the differential scanning calorimetry include PYRIS Diamond DSC (Perkin-Elmer), DSC 3200 (Bruker AXS) and the like.

Some measurement error is accepted also for the wave number in infrared absorption spectrum, and those skilled in the art readily understand that it is acceptable that values described in the specification may include such measurement errors. For example, according to the 4th edition of European Pharmacopoeia, in comparison with a reference spectrum in a confirmation test based on infrared absorption spectra, coincidence of wave number scale with a difference of ±0.5% or less is accepted. Although it is not intended to be bound by the aforementioned criterion in the specification, for example as an example of criterion, a measurement error of about ±0.8%, preferably about ±0.5%, particularly preferably about ±0.2%, is acceptable for the wave number scale.

Thermal stability of Compound 1 or the substance in the form of a salt can be evaluated by, for example, sealing a sample in a glass vial or the like, storing the vial under a severe temperature condition such as 40 to 80° C. in a dark place for a given period of time, and then observing or measuring appearance, purity, water content and the like of Compound 1 or the substance in the form of a salt. Change of purity before and after storage especially serves as an important index of thermal stability. For example, the evaluation is preferably performed under a storage condition of 60° C.

Hygroscopicity of Compound 1 or the substance in the form of a salt can be evaluated by putting a sample on a glass weighing dish, storing the dish in a dark place for a given period of time in an open state at a temperature of 25 to 40° C. under a humidification condition of about 75 to 94% relative humidity, and then observing or measuring appearance, purity, water content and the like of Compound 1 or the substance in the form of a salt. Increase of water content before and after storage especially serves as an important hygroscopic index. For example, the evaluation is preferably performed after storage conditions of 25° C. and 84% RH.

If a composition containing the monohydrochloride satisfies the conditions; 1) the ratio of the monohydrochloride exceeds 0%, and 2) any effect of the monohydrochloride is observed when compared with a composition that is equivalent except for the content of the monohydrochloride being 0%, it should be understood that any of such composition falls within the scope of the present invention. Further, a composition in which even a trace amount of the monohydrochloride is detected falls within the scope of the present invention.

In a composition containing the monohydrochloride, when (S)-1-(4-chloro-5-isoquinolinesulfonyl)-3-(methylamino)pyrrolidine, salt thereof and solvate thereof are focused and a total mass thereof is considered to be 100%, a mass ratio of the monohydrochloride is generally preferred to be about 90% or more, more preferably near 100%.

From a viewpoint of control of hygroscopicity of a composition that also contains the dihydrochloride, when at least 20% of the monohydrochloride is contained, the hygroscopicity controlling effect can be observed. Therefore, the ratio of at least 20% or more is exemplified as a preferred embodiment.

Further, from a viewpoint of suppression of coloring of the composition that also contains the dihydrochloride with passage of time, the monohydrochloride is preferably contained in an amount of about 60% or more, and the content of about 80% or more is exemplified as a more preferred embodiment.

The same shall apply to a composition containing the monohydrobromide.

EXAMPLES

The present invention will be more specifically explained with reference to examples. However, the scope of the present invention is not limited by the following examples.

Example 1

(S)-1-(4-Chloro-5-isoquinolinesulfonyl)-3-(methylamino)pyrrolidine (S)-3-[N-(tert-butoxycarbonyl)-N-methylamino]-1-(4-chloro-5-isoquinolinesulfonyl)pyrrolidine (370 g) obtained by the method described in WO2007/026664 was suspended in a mixed solution of 2-propanol (740 ml) and water (1261 ml). This suspension was added with hydrochloric acid (35%, specific gravity: 1.18, 271 g, Kanamori Industry) at 23° C. with stirring, and the mixture was warmed to 59.5° C. to react for 2 hours with stirring. After completion of the reaction, the temperature of the reaction mixture was maintained at 26 to 28° C., adjusted to pH 8.47 by adding dropwise 2 mol/l aqueous sodium hydroxide (1350 ml) with stirring, and then added with (S)-1-(4-chloro-5-isoquinolinesulfonyl)-3-(methylamino)pyrrolidine (1.42 g) as seed crystals at 26.0° C. Further, the reaction mixture was left to cool to 18.0° C. over 20 hours and 40 minutes with stirring. After the stand for cooling, the reaction mixture gave pH of 8.18. The mixture was adjusted to pH 9.67 by adding 2 mol/l aqueous sodium hydroxide (150 ml). After stirring for 1 hour, the reaction mixture was cooled to 1.0° C. over 4 hours and 22 minutes, and the deposited solid was collected by suction filtration using a Buchner funnel (internal diameter: 240 mm, filter paper: No. 131). The pale brown wet solid obtained was dried under reduced pressure at 50° C. for 18 hours to obtain slightly brown crystals of the title compound (259.3 g).

Example 2

(S)-1-(4-Chloro-5-isoquinolinesulfonyl)-3-(methylamino)pyrrolidine (S)-1-(4-Chloro-5-isoquinolinesulfonyl)-3-(methylamino)pyrrolidine dihydrochloride (1.50 g) obtained by the method described in WO2007/026664 was dissolved in water (32 ml). This solution was vigorously stirred, and slowly added dropwise with 2 N aqueous sodium hydroxide (4.13 ml, Wako Pure Chemical Industries) under ice cooling. The resulting suspension was further stirred at room temperature for 1 hour, and added with dichloromethane (30 ml), and the organic layer was separated. The aqueous layer was extracted with dichloromethane (30 ml), and the combined organic layers were washed with water (50 ml) and dried over anhydrous magnesium sulfate. The solvent was evaporated under reduced pressure, and ethyl acetate (10 ml) and n-hexane (20 ml) were added to the residue. The deposited solid was collected by filtration and dried by warming at 50° C. for 20 hours under reduced pressure to obtain the title compound (1.07 g).

Example 3

(S)-1-(4-Chloro-5-isoquinolinesulfonyl)-3-(methylamino)pyrrolidine monohydrochloride (S)-1-(4-Chloro-5-isoquinolinesulfonyl)-3-(methylamino)pyrrolidine (150 g) obtained in Example 1 was suspended in 2-propanol (2400 ml), and the suspension was warmed to 61.5° C. to dissolve the compound. This solution was filtered by using a membrane filter (internal diameter: 90 mm, ADVANTEC PTFE, 0.2 µm), and the filtrate was added dropwise with 300 ml of a mixed solution of hydrochloric acid (35%, specific gravity: 1.18, 48.0 g, Kanamori Industry) and purified water (261.4 ml, Fukuju Pharmaceuticals) with maintaining the filtrate at 55° C. The mixture was stirred at 55° C. for 44 minutes, then cooled to 2.0° C. over 2 hours and 11 minutes, and further stirred for 1 hour and 28 minutes, and then the deposited crystals were separated by suction filtration using a Buchner funnel (internal diameter: 150 mm, filter paper: No. 5C). The pale brown wet crystals obtained were dried under reduced pressure at 50° C. for 14 hours and 35 minutes to obtain the title compound (152 g).

Example 4

(S)-1-(4-Chloro-5-isoquinolinesulfonyl)-3-(methylamino)pyrrolidine monohydrobromide (S)-1-(4-Chloro-5-isoquinolinesulfonyl)-3-(methylamino)pyrrolidine (100 mg) obtained in Example 1 was dissolved in ethanol (2.5 ml), and added with 48% hydrobromic acid (33.2 µL, Wako Pure Chemical Industries), and the mixture was stirred at room temperature for 17 hours. The reaction mixture was further added with ethanol (4 ml), and the deposited solid was collected by filtration and dried by warming at 60° C. for 24 hours under reduced pressure to obtain the title compound (93.5 mg).

Test Example 1

Nuclear Magnetic Resonance Spectrum ($^1$H-NMR)

The compound obtained by the method described in Example 1 was taken in an amount of 0.02 g, and dissolved in 0.6 ml of dimethyl sulfoxide-$d_6$ (deuterated solvent) containing 0.05% of tetramethylsilane as an internal reference substance, and the nuclear magnetic resonance spectrum was measured under the following conditions. The substance gave peaks at δ (ppm): 1.95 (1H, m), 2.13-2.19 (2H, m), 2.33 (3H, s), 3.31-3.33 (2H, m), 3.49-3.53 (3H, m), 7.84-7.88 (1H, dd), 8.48-8.50 (1H, d), 8.63-8.65 (1H, d), 8.76 (1H, s), 9.41 (1H, s), and the $^1$H-$^1$H correlation of these peaks supported the structure of Compound 1.

The compound obtained by the method described in Example 3 was taken in an amount of 0.02 g, and dissolved in 0.6 ml of heavy water (deuterated solvent) containing 0.05% of sodium 3-trimethylsilylpropionate-$d_4$ as an internal reference substance, and the nuclear magnetic resonance spectrum was measured under the following conditions. The substance gave peaks at δ (ppm): 2.40-2.45 (1H, m), 2.70-2.75 (1H, m), 2.90 (3H, s), 3.65-3.71 (1H, m), 3.78-3.85 (2H, m), 3.96-4.01 (1H, m), 4.16-4.19 (1H, m), 4.33 (3H, s), 7.62-7.66 (1H, dd), 8.05-8.09 (2H, dd), 8.40 (1H, s), 8.83 (1H, s), and the $^1$H-$^1$H correlation of these peaks supported the structure of the monohydrochloride.
Conditions:
Nuclear magnetic resonance apparatus: JNM LA400 (JEOL)
Oscillation frequency: 400 MHz
Nuclide: $^1$H Test Example 2

Mass Spectrum

Mass spectrum of the compound obtained by the method described in Example 1 was measured under the following conditions, and a protonated molecule was detected at (m/z)=326, which result supported the structure of Compound 1.
Mass spectrum of the compound obtained by the method described in Example 3 was measured under the following conditions, and a protonated molecule was detected at (m/z)=326, which result supported the structure of the monohydrochloride.
Conditions:
Mass spectrometer: JMS-SX102 (JEOL)
Ionizing method: FAB
Detected ion: Cation
Dissolution solvent: Dimethyl sulfoxide
Matrix: m-Nitrobenzyl alcohol Test Example 3

Differential Scanning Calorimetry

Figure 2:
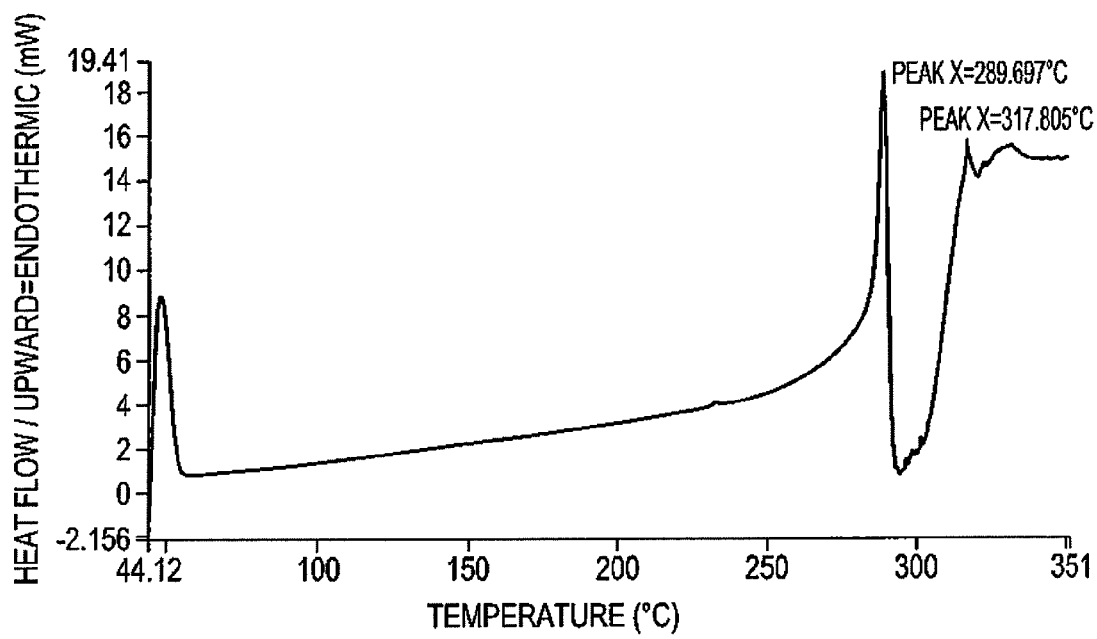
FIG. 2 A figure depicting differential scanning calorimetry spectrum of the monohydrochloride obtained by the method described in Example 3
Figure 3:
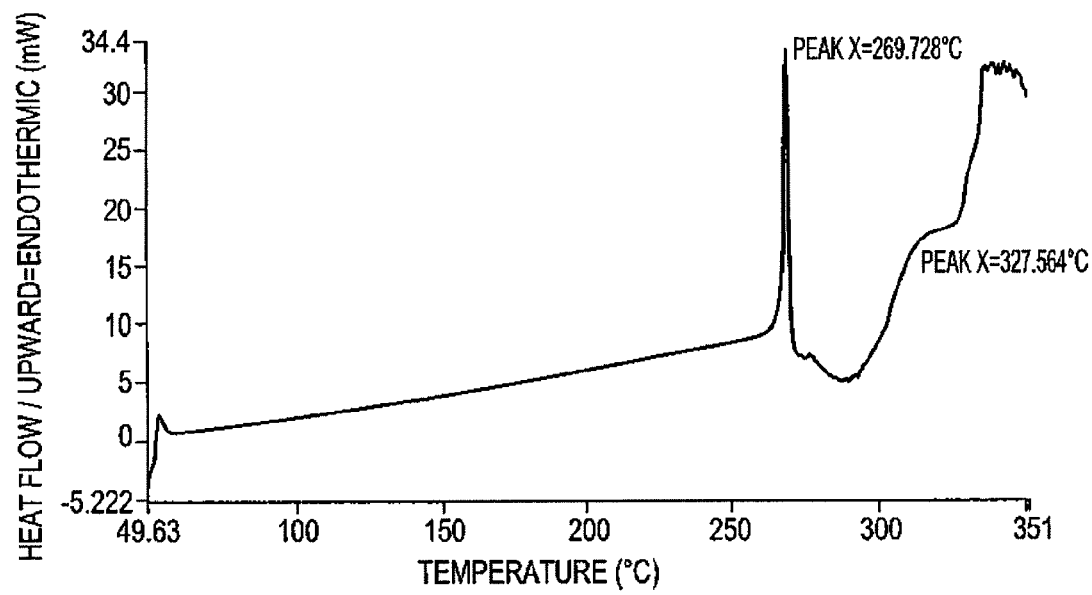
FIG. 3 A figure depicting differential scanning calorimetry spectrum of the monohydrobromide obtained by the method described in Example 4

Differential scanning calorimetry of the compound obtained by a method similar to the method described in Example 1 was performed under the following conditions, and the spectrum shown in FIG. 1 was obtained, in which a thermal absorption peak considered to be a fusion peak was observed at 107° C.
Conditions:
Calorimeter: PYRIS Diamond DSC
Temperature increasing condition: Increase from 50° C. to 250° C. at a rate of 10° C./minute
Differential scanning calorimetry of the compound obtained by the method described in Example 3 was performed under the following conditions, and the spectrum shown in FIG. 2 was obtained, in which a thermal absorption peak considered to be a resolution peak was observed at 290° C.
Conditions:
Calorimeter: PYRIS Diamond DSC
Temperature increasing condition: Increase from 50° C. to 350° C. at a rate of 10° C./minute
Differential scanning calorimetry of the compound obtained by the method described in Example 4 was performed under the following conditions, and the spectrum shown in FIG. 3 was obtained, in which a thermal absorption peak considered to be a resolution peak was observed at 270° C.
Conditions
Calorimeter: PYRIS Diamond DSC
Temperature increasing condition: Increase from 50° C. to 350° C. at a rate of 10° C./minute Test Example 4

Ion Exchange Chromatography

When the compound obtained by the method described in Example 1 was analyzed by ion exchange chromatography under the following conditions, fluoride ion, chloride ion, bromide ion, nitrite ion, nitrate ion, phosphate ion, sulfate ion and other anions were not detected, and thus it was confirmed that the compound obtained by the method described in Example 1 was (S)-1-(4-chloro-5-isoquinolinesulfonyl)-3-(methylamino)pyrrolidine (Compound 1).
When salt number of the compound obtained by the method described in Example 3 was confirmed by ion exchange chromatography under the following conditions, 1.0 of chloride ion was observed per molecule of (S)-1-(4-chloro-5-isoquinolinesulfonyl)-3-(methylamino)pyrrolidine, and thus it was confirmed that the substance was a salt of (S)-1-(4-chloro-5-isoquinolinesulfonyl)-3-(methylamino)pyrrolidine (Compound 1) added with one hydrochloric acid (monohydrochloride).
When salt number of the compound obtained by the method described in Example 4 was confirmed by ion exchange chromatography under the following conditions, 1.0 of bromide ion was observed per molecule of (S)-1-(4-chloro-5-isoquinolinesulfonyl)-3-(methylamino)pyrrolidine, and thus it was confirmed that the substance was a salt of (S)-1-(4-chloro-5-isoquinolinesulfonyl)-3-(methylamino) pyrrolidine (Compound 1) added with one hydrobromic acid (monohydrobromide).
Conditions:
Sample concentration: 100 μg/ml
Ion chromatograph: DIONEX ICS-1000 (Dionex Japan)
Detector: Electric conductivity detector
Column: DIONEX IonPacAS14, internal diameter: 4 mm, length: 25 cm
Guard column: DIONEX IonPacAG14, internal diameter: 4 mm, length: 5 cm
Column temperature: 30° C.
Mobile phase: 1.0 mmol/l Aqueous sodium hydrogencarbonate containing 3.5 mmol/l sodium carbonate
Flow rate: About 1.2 ml/minute
Injection: 10 μl
Suppressor: ASRS-ULTRA (recycling mode, SRS 24 mA)

Test Example 5

Powder X-Ray Diffractometry

Figure 4:
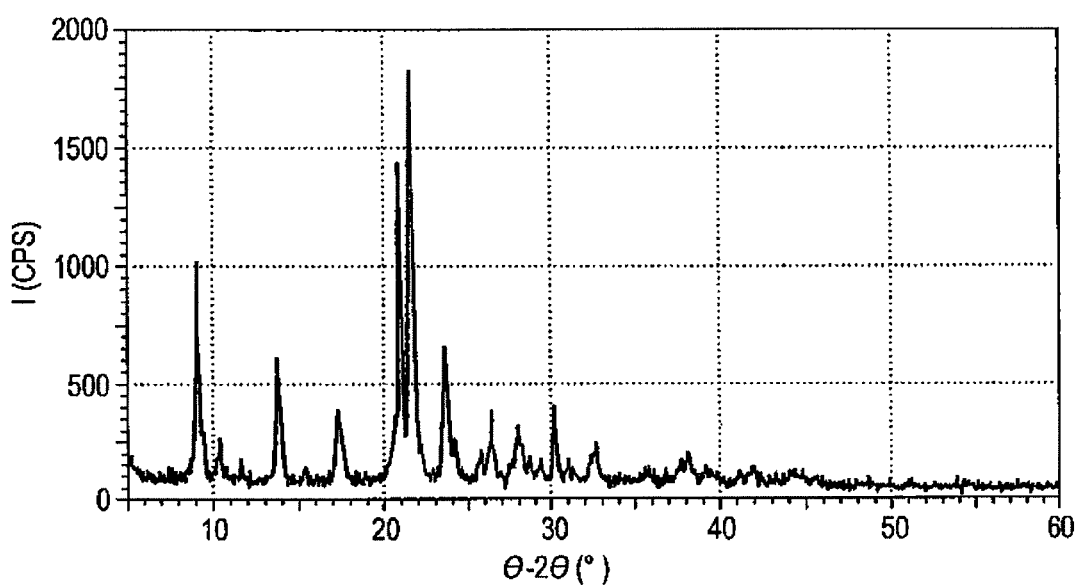
FIG. 4 A figure depicting powder X-ray diffraction spectrum of Compound 1 obtained by the method described in Example 1
Figure 5:
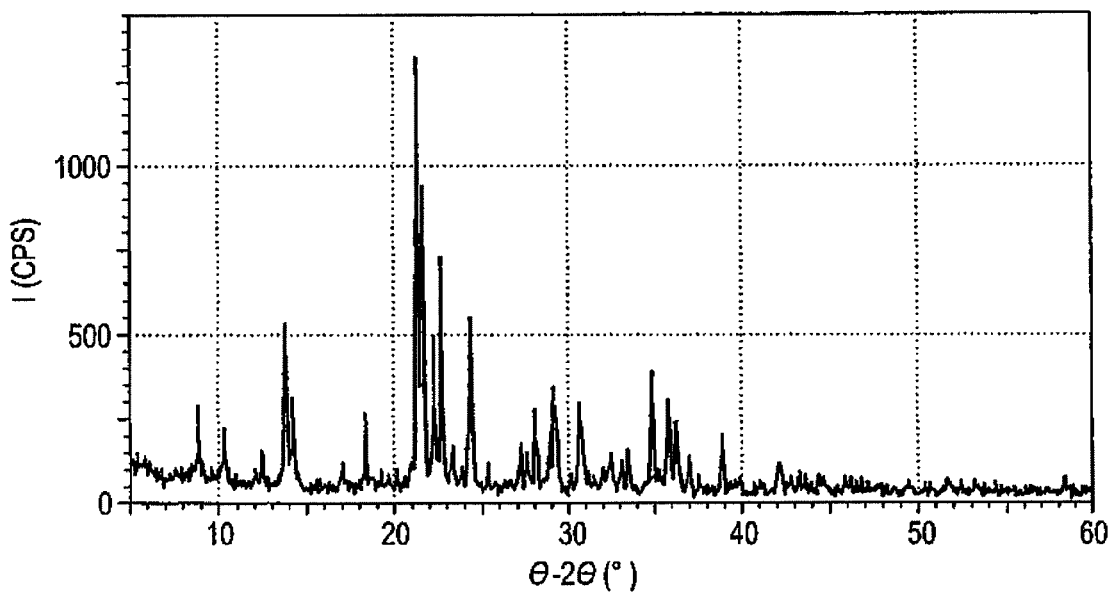
FIG. 5 A figure depicting powder X-ray diffraction spectrum of the monohydrochloride obtained by the method described in Example 3

Powder X-ray diffractometry of the compound obtained by the method described in Example 1 was performed under the following conditions, and the diffraction spectrum shown in FIG. 4 was obtained. In this powder X-ray diffraction spectrum, characteristic major peaks were observed at the positions where 2θs are 9.1°, 13.8°, 21.0°, 21.7° and 23.6°. Peaks were also observed at the positions of 17.4°, 20.5°, 26.3°, 28.0° and 30.2°, and any one or more of these peaks are also considered to be a peak or peaks characteristic to Compound 1. Furthermore, peaks were also observed at the positions of 24.1°, 25.7°, 28.7°, 32.7°, 38.3° and 42.0°, and any one or more of these peaks can also be considered to be a peak or peaks characteristic to Compound 1.
Powder X-ray diffractometry of the monohydrochloride obtained by the method described in Example 3 was performed under the following conditions, and the diffraction spectrum shown in FIG. 5 was obtained. In this powder X-ray diffraction spectrum, characteristic major peaks were observed at the positions where 2θs are 13.9°, 21.5°, 21.7°, 22.4°, 22.8°, 24.5° and 35.0°. Peaks were also observed at the positions of 14.3°, 28.2°, 29.3°, 30.8° and 36.0°, and any one or more of these peaks can also be considered to be a peak or peaks characteristic to the monohydrochloride. Furthermore, peaks were also observed at the positions of 8.9°, 18.4°, 36.4° and 39.1°, and any one or more of these peaks can also be considered to be a peak or peaks characteristic to the monohydrochloride.

Figure 6:
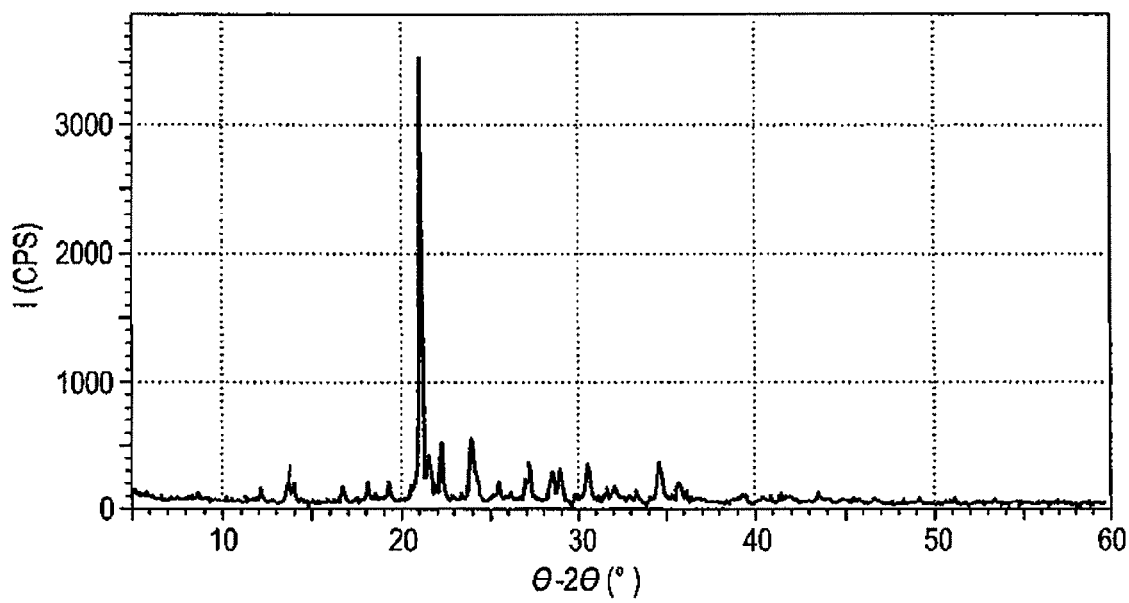
FIG. 6 A figure depicting powder X-ray diffraction spectrum of the monohydrobromide obtained by the method described in Example 4

Powder X-ray diffractometry of the monohydrobromide obtained by the method described in Example 4 was performed under the following conditions, and the diffraction spectrum shown in FIG. 6 was obtained. In this powder X-ray diffraction spectrum, characteristic major peaks were observed at the positions where 2θs are 21.3°, 22.4°, 24.1°, 30.7° and 34.8°. Peaks were also observed at the positions of 13.8°, 21.7°, 27.3°, 28.6° and 29.1°, and any one or more of these peaks can also be considered to be a peak or peaks characteristic to the monohydrobromide. Furthermore, peaks were also observed at the positions of 16.8°, 19.4°, 25.6°, 27.1° and 36.0°, and any one or more of these peaks can also be considered to be a peak or peaks characteristic to the monohydrobromide.

Figure 7:
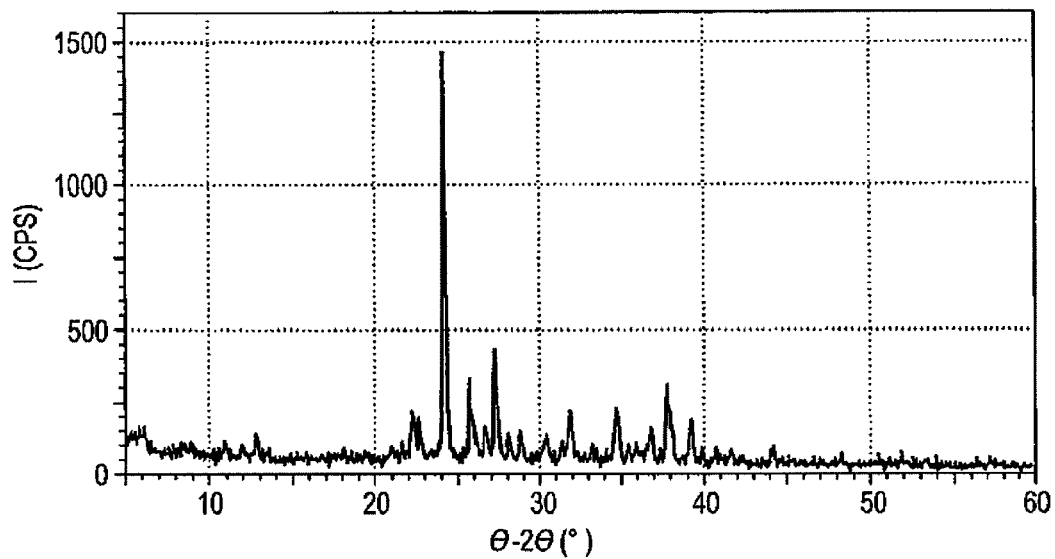
FIG. 7 A figure depicting powder X-ray diffraction spectrum of the dihydrochloride FIG. 8 A figure depicting infrared absorption spectrum of Compound 1 obtained by the method described in Example 1

Compound 1, the monohydrochloride, and the monohydrobromide were judged to be crystals by visual inspection, and they were further confirmed to be crystals by the aforementioned powder X-ray diffraction analysis. It was also confirmed that Compound 1, the monohydrochloride, and the monohydrobromide gave powder X-ray diffraction spectra different from that of the dihydrochloride shown in FIG. 7.

Measurement Conditions:
X-Ray diffractometer: XRD-6000 (Shimadzu) or RINT 2200 Ultima+/PC (Rigaku International)
X-Ray source: CuKα (40 kV, 30 mA)
Operation mode: Continuous
Scanning speed: 2°/minute
Scanning axis: θ to 2θ
Scanning range: 5 to 60°
Scattering slit: 1°
Light-receiving slit: 0.30 mm Test Example 6

Infrared Absorption Spectrum

Figure 8:
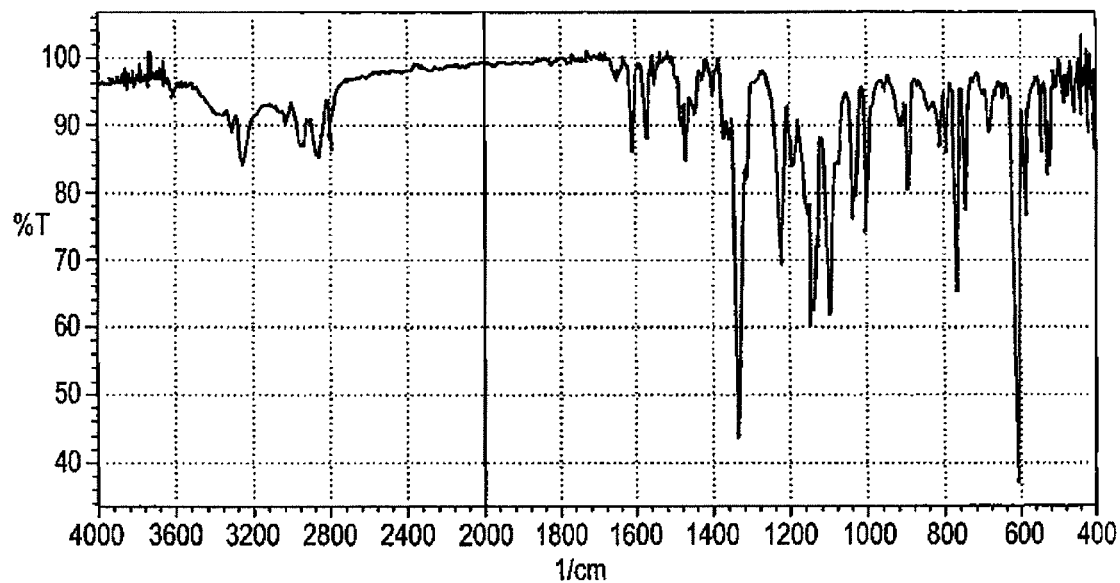

Infrared absorption spectrum of Compound 1 obtained by the method described in Example 1 was measured under the following conditions, and the spectrum shown in FIG. 8 was obtained. In this infrared absorption spectrum, characteristic absorptions were observed at the positions where wave numbers are 1335, 1146, 1139, 1096 and 609 $cm^{-1}$. Absorptions were also observed at the positions of 1219, 1156, 1130, 1033, 1027, 1000, 766, 742 and 584 $cm^{-1}$, and any one or more of these absorptions can be considered to be a characteristic absorption or absorptions of Compound 1.

Figure 9:
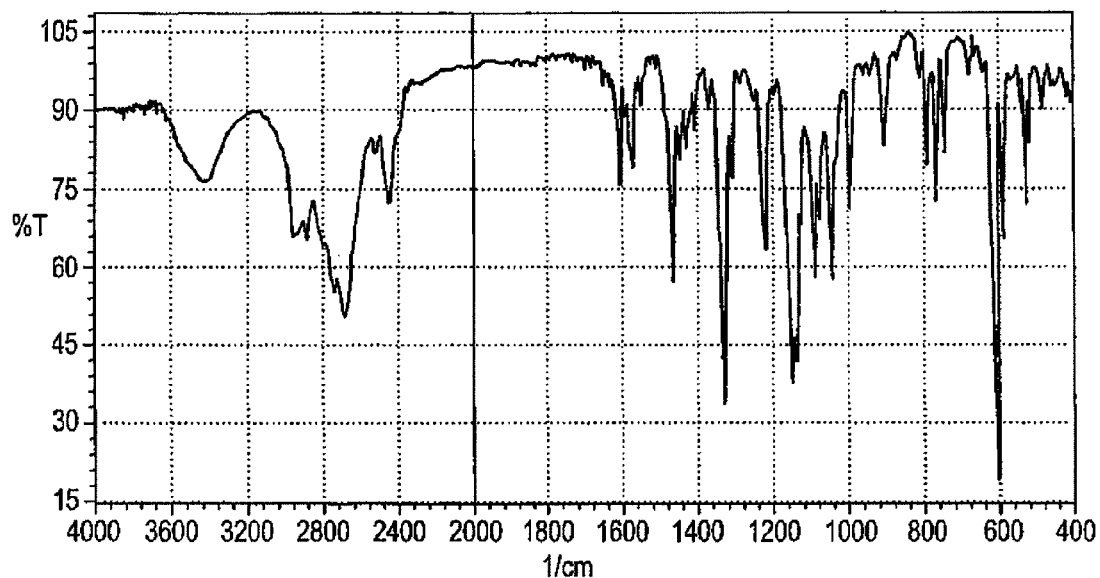
FIG. 9 A figure depicting infrared absorption spectrum of the monohydrochloride obtained by the method described in Example 3

Infrared absorption spectrum of the monohydrochloride obtained by the method described in Example 3 was measured under the following conditions, and the spectrum shown in FIG. 9 was obtained. In this infrared absorption spectrum, characteristic absorptions were observed at the positions where wave numbers are 1330, 1150, 1140 and 613 $cm^{-1}$. Absorptions were also observed at the positions of 2747, 2695, 2690, 1487, 1091 and 1046 $cm^{-1}$, and any one or more of these absorptions can be considered to be a characteristic absorption or absorptions of the monohydrochloride.

Figure 10:
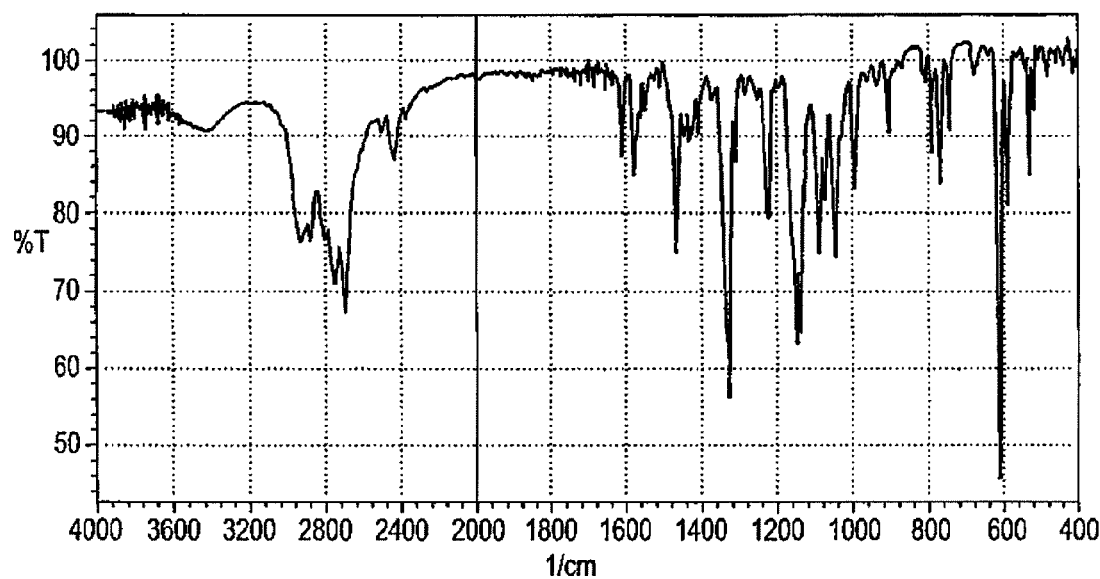
FIG. 10 A figure depicting infrared absorption spectrum of the monohydrobromide obtained by the method described in Example 4

Infrared absorption spectrum of the monohydrobromide obtained by the method described in Example 4 was measured under the following conditions, and the spectrum shown in FIG. 10 was obtained. In this infrared absorption spectrum, characteristic absorptions were observed at the positions where wave numbers are 2695, 1307, 1149, 1139 and 612 $cm^{-1}$. Absorptions were also observed at the positions of 2963, 2932, 2916, 2909, 2880, 2807, 2795, 2751, 1466, 1222, 1219, 1089 and 1044 $cm^{-1}$, and any one or more of these absorptions can be considered to be a characteristic absorption or absorptions of the monohydrobromide.

Figure 11:
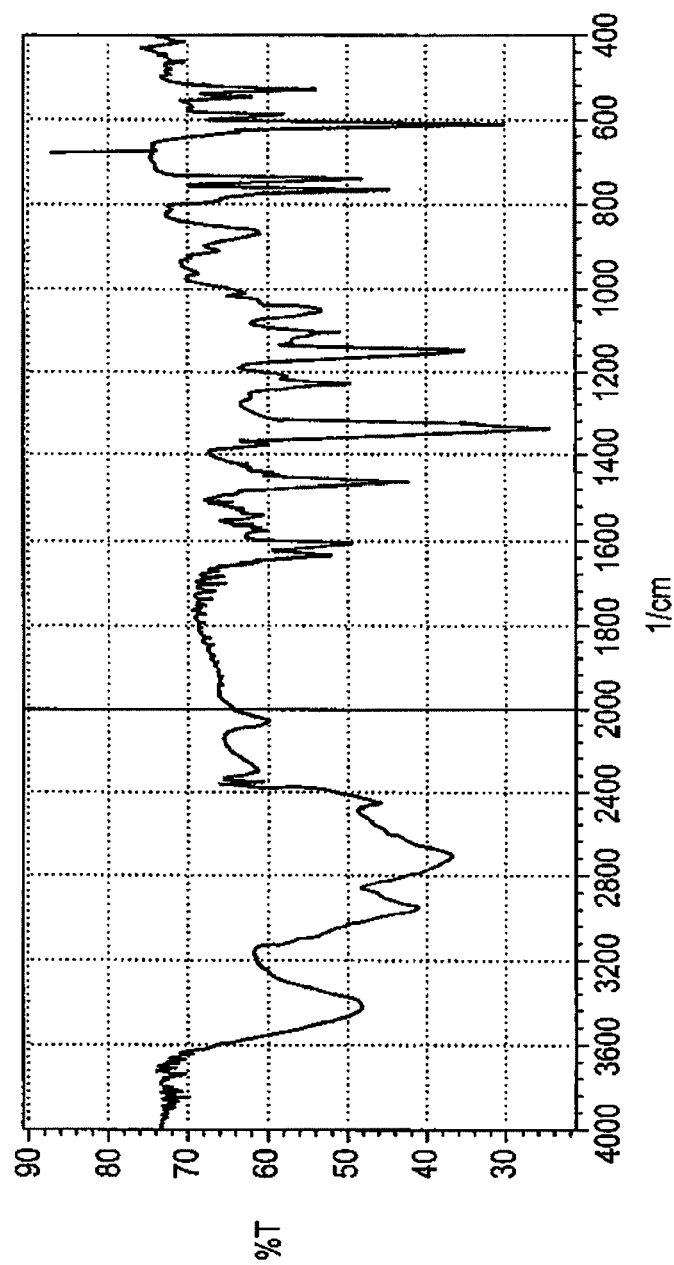
FIG. 11 A figure depicting infrared absorption spectrum of the dihydrochloride

It was also confirmed that Compound 1, the monohydrochloride, and the monohydrobromide gave spectra different from the infrared absorption spectrum of the dihydrochloride shown in FIG. 11.

Measurement Conditions:
Infrared spectrophotometer: FTIR-8300 (Shimadzu)
Measurement method: Potassium bromide tablet method
Control: Potassium bromide tablet
Gain: Auto
Aperture: Auto
Minimum wave number: 400 $cm^{-1}$
Maximum wave number: 4000 $cm^{-1}$
Number of integration: 45 times
Detector: Standard
Apodization function: Happ-Genzel
Decomposition: 2 $cm^{-1}$
Mirror velocity: 2.8

Test Example 7

Purity Test

Purity of Compound 1 obtained by the method described in Example 1 was measured by high performance liquid chromatography under the following conditions. As a result, a peak of (S)-1-(4-chloro-5-isoquinolinesulfonyl)-3-(methylamino)pyrrolidine was observed at from 12 to 13 minutes, and the purity was found to be 99.9%.

Purity of the monohydrochloride obtained by the method described in Example 3 was similarly measured. As a result, a peak of (S)-1-(4-chloro-5-isoquinolinesulfonyl)-3-(methylamino)pyrrolidine was observed at from 12 to 13 minutes, and the purity was found to be 99.4%.

Purity of the monohydrobromide obtained by the method described in Example 4 was similarly measured. As a result, a peak of (S)-1-(4-chloro-5-isoquinolinesulfonyl)-3-(methylamino)pyrrolidine was observed at from 12 to 13 minutes, and the purity was found to be 99.7%.

Conditions of High Performance Liquid Chromatography:
High performance liquid chromatography apparatus: LC-10A Series (Shimadzu) or Agilent 1100 series (Agilent Technologies)
Solution concentration: 500 µg/ml
Injection: 10 µl
Detector: Ultraviolet absorptiometer (measurement wavelength: 245 nm)
Column: XBridge Shield RP18 5 µm, internal diameter: 4.6 mm, length: 15 cm (Waters)
Column temperature: Constant temperature around 40° C.
Mobile phase A: 20 mmol/l Sodium phosphate buffer (pH 7.0)

Mobile phase B: Acetonitrile
Liquid feeding program: A concentration gradient was formed by changing the mixing ratio of the mobile phase A and the mobile phase B as shown in Table 1.
Flow rate: 1.0 ml/minute

TABLE 1

Liquid feeding program

| Time from injection (minute) | Mobile phase A (%) | Mobile phase B (%) |
|---|---|---|
| 0 to 45.5 | 80 → 15 | 20 → 85 |
| 45.5 to 54 | 15 | 85 |
| 54 to 69 | 80 | 20 |

Dissolution solvent: Mixture of water/methanol (1:1)

Test Example 8

Measurement of Water Content

Water content of the monohydrochloride obtained by the method described in Example 3 and the monohydrobromide obtained by the method described in Example 4 was measured according to the "coulometric titration method" defined in Japanese Pharmacopoeia, General Test Methods, "Water Determination" under the following conditions, and water contents of the monohydrochloride was found to be 0.20% and that of the monohydrobromide was found to be 0.14%.
Conditions:
Water content measurement apparatus: AQ-7 (Hiranuma Sangyo)
Sample amount: 5 mg
Anolyte: Aqualyte RS (Sigma-Aldrich)
Catholyte: Aqualyte CN (Sigma-Aldrich)

Test Example 9

Thermal Stability Test

The monohydrochloride obtained by the method described in Example 3, the monohydrobromide obtained by the method described in Example 4, and the dihydrochloride as a control were weighed in a glass vial in an amount of 40 mg each, and the glass vial was sealed. Each sample was stored in a dark place at 60° C. for 2 to 4 weeks, and after the storage, appearance was evaluated by visual inspection. Further, purity was measured under the conditions of Test Example 7, and water content was measured under the conditions of Test Example 8.

The dihydrochloride gave change of appearance after the storage at 60° C. for 2 weeks. Whilst, the monohydrochloride and the monohydrobromide gave no change of appearance and no degradation of purity even after the storage at 60° C. for 4 weeks.

TABLE 2

| Salt | Test | Before storage | After 2 weeks | After 4 weeks |
|---|---|---|---|---|
| Monohydrochloride | Appearance | White powder | White powder | White powder |
|  | Water content | 0.20% | 0.06% | 0.08% |
|  | Purity | 99.4% | 99.9% | 99.7% |
| Monohydrobromide | Appearance | White powder | White powder | White powder |

TABLE 2-continued

| Salt | Test | Before storage | After 2 weeks | After 4 weeks |
|---|---|---|---|---|
|  | Water content | 0.14% | 0.05% | 0.05% |
|  | Purity | 99.7% | 99.9% | 99.8% |
| Dihydrochloride | Appearance | White powder | Pale brown powder | —* |
|  | Water content | 3.76% | 2.93% | —* |
|  | Purity | 98.1% | 99.5% | —* |

*The dihydrochloride gave apparent change of appearance after 2 weeks, and therefore the stability test was terminated.

Test Example 10

Hygroscopicity Test 1

The monohydrochloride obtained by the method described in Example 3, the monohydrobromide obtained by the method described in Example 4, and the dihydrochloride as a control were weighed on a glass weighing dish in an amount of 40 mg each, and each sample was stored in a dark place at 25° C. and 84% RH for 2 to 4 weeks. After the storage, appearance was evaluated by visual inspection. Further, purity was measured under the conditions of Test Example 7, and water content was measured under the conditions of Test Example 8.

The dihydrochloride gave apparent change of appearance and marked moisture absorption after the storage at 25° C. and 84% RH for 2 weeks. Whilst, the monohydrochloride and the monohydrobromide gave no change of appearance as well as no substantial increase of water content and no degradation of purity even after the storage at 25° C. and 84% RH for 4 weeks.

It was confirmed by Test Examples 9 and 10 that the monohydrochloride and the monohydrobromide have more satisfactory thermal stability and remarkably lower hygroscopicity compared with the dihydrochloride.

TABLE 3

| Salt | Test | Before storage | After 2 weeks | After 4 weeks |
|---|---|---|---|---|
| Monohydrochloride | Appearance | White powder | White powder | White powder |
|  | Water content | 0.20% | 0.23% | 0.26% |
|  | Purity | 99.4% | 99.8% | 99.6% |
| Monohydrobromide | Appearance | White powder | White powder | White powder |
|  | Water content | 0.14% | 0.05% | 0.05% |
|  | Purity | 99.7% | 99.9% | 99.7% |
| Dihydrochloride | Appearance | White powder | Brown powder | —** |
|  | Water content | 3.76% | 15.24% | —** |
|  | Purity | 98.1% | 99.3% | —** |

**The dihydrochloride showed definite change of appearance and marked moisture absorption after 2 weeks, and therefore the stability test was terminated.

Test Example 11

Hygroscopicity Test 2

Compound 1 obtained by a method similar to the method described in Example 1 (two kinds of lots), the monohydrochloride obtained by the method described in Example 3, the dihydrochloride, and mixtures of the monohydrochloride and the dihydrochloride at ratios of 9:1, 8:2, 6:4, 4:6 and 2:8 were weighed on a glass weighing dish in an amount of each 40 mg, and each sample was stored in a dark place at 25° C. and 84%

RH for 2 to 4 weeks. After the storage, appearance was evaluated by visual inspection. Further, purity was measured under the conditions of Test Example 7, and water content was measured under the conditions of Test Example 8.

Both of the two lots of Compound 1 gave moisture absorption after the storage at 25° C. and 84% RH for 2 weeks, and further moisture absorption after the storage at 25° C. and 84% RH for 4 weeks.

The mixtures of the monohydrochloride and the dihydrochloride containing the dihydrochloride at a ratio of 40% or more gave apparent change of appearance after the storage at 25° C. and 84% RH for 2 weeks. It was also observed that a higher ratio of the dihydrochloride gave higher hygroscopicity.

It was confirmed by Test Example 11 that the monohydrochloride had a hygroscopicity lower than any of Compound 1 (free base) and mixtures of the monohydrochloride and the dihydrochloride. Moreover, it was also confirmed that, in a mixture of the dihydrochloride and the monohydrochloride, increase of the mixing ratio of the monohydrochloride lowered the hygroscopicity of the mixture.

TABLE 4

| Salt | Test | Before storage | After 2 weeks | After 4 weeks |
|---|---|---|---|---|
| Compound 1 (Lot 1) | Appearance | Slightly brownish white powder | Slightly brownish white powder | Slightly brownish white powder |
| | Water content | 0.9% | 5.7% | 8.1% |
| | Purity | 99.9% | 99.9% | 99.9% |
| Compound 1 (Lot 2) | Appearance | Slightly brownish white powder | Slightly brownish white powder | Slightly brownish white powder |
| | Water content | 1.7% | 7.6% | 9.1% |
| | Purity | 99.9% | 99.9% | 99.9% |
| Monohydrochloride | Appearance | White powder | White powder | —*** |
| | Water content | 0.0% | 0.1% | —*** |
| | Purity | 100.0% | 100.0% | —*** |
| Dihydrochloride | Appearance | White powder | Pale yellow powder | —*** |
| | Water content | 5.2% | 19.8% | —*** |
| | Purity | 100.0% | 99.9% | —*** |
| Monohydrochloride:Dihydrochloride Mixing ratio 9:1 | Appearance | White powder | White powder | —*** |
| | Water content | 0.7% | 2.1% | —*** |
| | Purity | 100.0% | 100.0% | —*** |
| Monohydrochloride:dihydrochloride Mixing ratio 8:2 | Appearance | White powder | White powder | —*** |
| | Water content | 0.9% | 6.6% | —*** |
| | Purity | 100.0% | 100.0% | —*** |
| Monohydrochloride:dihydrochloride Mixing ratio 6:4 | Appearance | White powder | Slightly yellowish white powder | —*** |
| | Water content | 1.7% | 11.2% | —*** |
| | Purity | 100.0% | 99.9% | —*** |
| Monohydrochloride:dihydrochloride Mixing ratio 4:6 | Appearance | White powder | Pale yellow powder | —*** |
| | Water content | 4.3% | 16.8% | —*** |
| | Purity | 100.0% | 99.9% | —*** |
| Monohydrochloride:dihydrochloride Mixing ratio 2:8 | Appearance | White powder | Pale yellow powder | —*** |
| | Water content | 4.3% | 18.4% | —*** |
| | Purity | 100.0% | 99.9% | —*** |

***Test was not performed.

INDUSTRIAL APPLICABILITY (S)-1-(4-Chloro-5-isoquinolinesulfonyl)-3-(methylamino)pyrrolidine monohydrochloride and (S)-1-(4-chloro-5-isoquinolinesulfonyl)-3-(methylamino)pyrrolidine monohydrobromide provided by the present invention are characterized in that they are highly stable and have low hygroscopicity. Therefore, these substances are useful as active ingredients of medicaments, of which decrease in content of the active ingredient during storage or distribution is suppressed, and also useful for stable supply of medicaments for which efficacy and safety can be ensured over a long period of time.

What is claimed is:

1. The crystal of (S)-1-(4-chloro-5-isoquinolinesulfonyl)-3-(methylamino)pyrrolidine, which has a major peak or peaks at one or more positions selected from the group consisting of positions where 2θs are about 9.1°, 13.8°, 21.0°, 21.7° and 23.6° in a powder X-ray diffraction spectrum.

2. The crystal of (S)-1-(4-chloro-5-isoquinolinesulfonyl)-3-(methylamino)pyrrolidine according to claim 1, which has major peaks at positions where 2θs are about 9.1°, 13.8°, 21.0°, 21.7° and 23.6° in a powder X-ray diffraction spectrum.

3. The crystal of (S)-1-(4-chloro-5-isoquinolinesulfonyl)-3-(methylamino)pyrrolidine according to claim 2, which has major peaks at positions where wave numbers are about 1335, 1146, 1139, 1096 and 609 cm-1 in an infrared absorption spectrum.

4. The crystal of (S)-1-(4-chloro-5-isoquinolinesulfonyl)-3-(methylamino)pyrrolidine according to claim 3, which has a fusion peak at about 106° in differential scanning calorimetry (temperature increasing rate: 10° C./minute).

5. A method for preparing the crystal of (S)-1-(4-chloro-5-isoquinolinesulfonyl)-3-(methylamino)pyrrolidine according to any one of claims 1 to 4, which comprises the steps of adding a base to an acidic solution containing (S)-1-(4-chloro-5-isoquinolinesulfonyl)-3-(methylamino)pyrrolidine to neutralize the solution, wherein said compound is prepared by reacting (S)-3[N-(tert-butoxycarbonyl)-N-methylamino]-1-(4-chloro-5-isoquinolinesulfonyl)pyrrolidine with an acid in a solvent, and isolating a deposited solid.

6. A method for preparing the crystal of (S)-1-(4-chloro-5-isoquinolinesulfonyl)-3-(methylamino)pyrrolidine according to any one of claims 1 to 4, which comprises the steps of adding a base to a solution of dihydrohalide of (S)-1-(4-chloro-5-isoquinolinesulfonyl)-3-(methylamino)pyrrolidine to neutralize the solution and thereby prepare (S)-1-(4-chloro-5-isoquinolinesulfonyl)-3-(methylamino)pyrrolidine, and isolating a solid of the compound deposited in a poor solvent in which the compound is hardly dissolved.

7. The (S)-1-(4-chloro-5-isoquinolinesulfonyl)-3-(methylamino)pyrrolidine according to claim 1, which is at least 99.9% pure.

8. A pharmaceutical composition comprising the crystal according to claim 1.

9. A method of lowering intraocular pressure which comprises administering to a patient in need thereof an effective amount of the crystal according to claim 1.

10. A method of treating glaucoma which comprises administering to a patient in need thereof an effective amount of the crystal according to claim 1.

* * * * *